US00PP16968P2

(12) United States Plant Patent
Pieters

(10) Patent No.: US PP16,968 P2
(45) Date of Patent: Aug. 8, 2006

(54) ***CHRYSANTHEMUM* PLANT NAMED 'PPP MIL PK05'**

(50) Latin Name: *Chrysanthemum morifolium*
Varietal Denomination: PPP MIL PK05

(75) Inventor: Dirk Pieters, Ooostnieuwkerke (BE)

(73) Assignee: Pieters Plant Production, BVBA, Oosnieuwkerke (BE)

( * ) Notice: Subject to any disclaimer, the term of this patent is extended or adjusted under 35 U.S.C. 154(b) by 0 days.

(21) Appl. No.: 11/115,704

(22) Filed: Apr. 27, 2005

(51) Int. Cl.
*A01H 5/00* (2006.01)

(52) U.S. Cl. ..... Plt./291

(58) Field of Classification Search ..... Plt./291
See application file for complete search history.

*Primary Examiner*—Kent Bell
*Assistant Examiner*—Annette H Para
(74) *Attorney, Agent, or Firm*—Albert O. Cota

(57) ABSTRACT

A new and distinct *Chrysanthemum* plant cultivar is disclosed, characterized by large decorative type inflorescences, consistent flowering response to short days, blooming consistently after 49 days of short day length, pink two tone ray florets, free branching habit, and a consistent natural season flowering habit during early September.

1 Drawing Sheet

Figure 1:
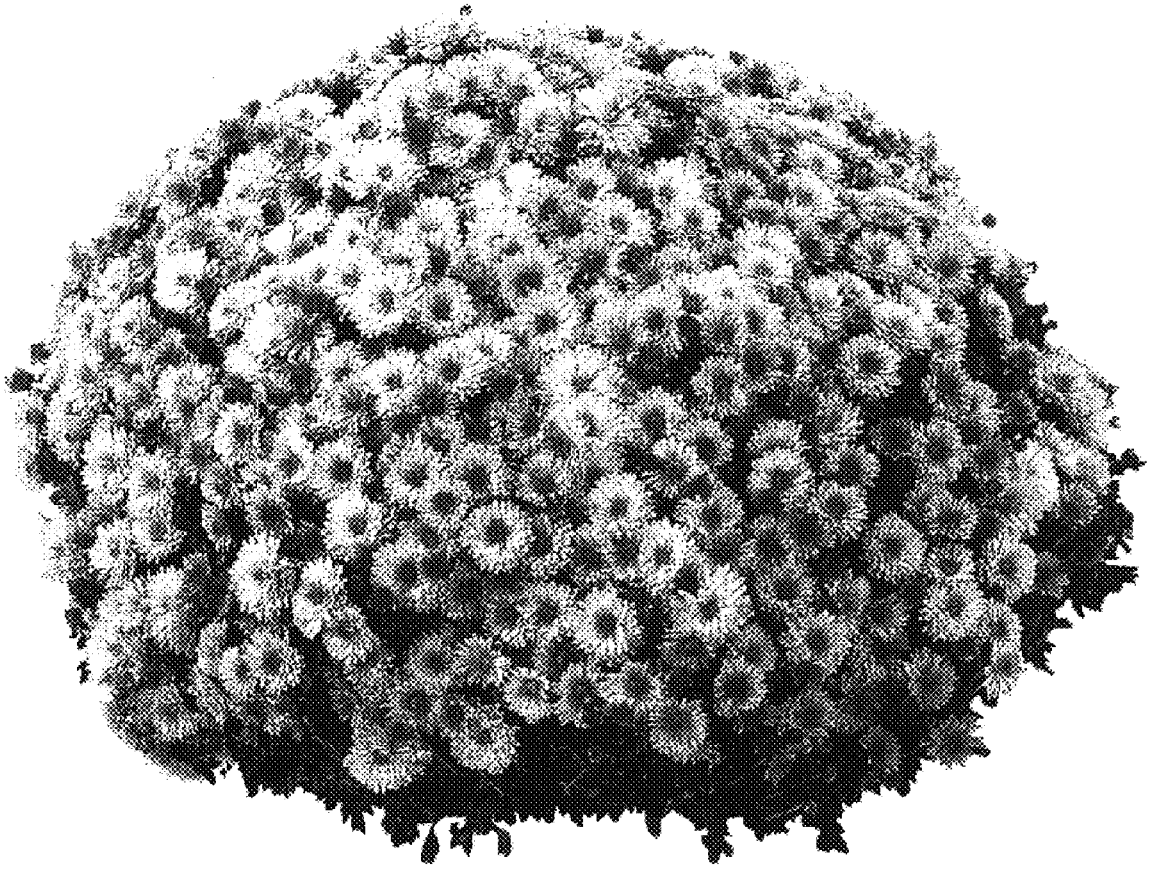

Latin name of the genus and species: *Chrysanthemum morifolium.*
Variety denomination: 'PPP MIL PK05'.

BACKGROUND OF THE INVENTION

The new cultivar 'PPP MIL PK05' is a product of induced mutation of the parent *Chrysanthemum* plant variety 'GEDI THREE MIL', U.S. Plant patent application Ser. No. 11/118,273, using gamma ray treatment at a dose of 20 Gy. The new cultivar was discovered and selected by Dirk Pieters in September 2003 in Oostnieuwkerke, Belgium.

Asexual reproduction of the new cultivar 'PPP MIL PK05' by terminal cuttings and tissue culture was performed in Oostnieuwkerke, Belgium, and has shown that the unique features of this new cultivar are stable and reproduced true to type on successive generations.

SUMMARY OF THE INVENTION

The cultivar 'PPP MIL PK05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP MIL PK05.' These characteristics in combination distinguish 'PPP MIL PK05' as a new and distinct *Chrysanthemum* cultivar:

1. Pink two-tone decorative type inflorescence;
2. Consistent flowering response to short days, blooming consistently after 49 days of short day length;
3. Free branching habit; and
4. Consistent natural season flowering habit in early September.

Plants of the new cultivar 'PPP MIL PK05' are similar to plants of the parent variety, 'GEDI THREE MIL' in most horticultural characteristics, however the new cultivar 'PPP MIL PK05' is taller than the parent and has more ray florets. Additionally, the new variety 'PPP MIL PK05' has different color ray florets than the parent 'GEDI THREE MIL'.

In comparison to the commercially available variety 'GEDI TWO CAN' (U.S. Plant Pat. No. 14,474), 'PPP MIL PK05' has a darker center in the bloom. Additionally, the new variety 'PPP MIL PK05' naturally blooms approximately fifteen days earlier than the comparable variety. Further, the new variety 'PPP MIL PK05' has a larger diameter inflorescence and has more inflorescence per flowering branch than the comparable variety 'GEDI TWO CAN.'

BRIEF DESCRIPTION OF THE PHOTOGRAPH

The accompanying photograph in FIG. 1 illustrates in full color a typical plant of 'PPP MIL PK05' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP MIL PK05' plants grown in Oxnard, Ventura County, Calif., during the month of September 2004. The growing temperature ranged from 12° C. to 15° C. at night to 12° C. to 20° C. during the day. Measurements and numerical values represent averages of typical flowering types.

Botanical classification: *Chrysanthemum morifolium* cultivar 'PPP MIL PK05.'
Commercial classification: Garden-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 31 cm.
Plant spread: Approximately 36 cm.
Growth rate: Moderate.
Branching characteristics: Free Branching.
Length of lateral branches: Approximately 27 cm.
Number of leaves per lateral branch: Approximately 25.
Age of plant described: Approximately 148 days.

FOLIAGE

Leaf:
*Arrangement*.—Alternate single.
*Average length*.—Approximately 6.9 cm.
*Average width*.—Approximately 5.2 cm.
*Shape of blade*.—Ovate.
*Apex*.—Cuspidate.
*Base*.—Attenuate.
*Attachment*.—Stalked.
*Margin*.—Palmately lobed and toothed.
*Texture of top surface*.—Lightly pubescent.
*Texture of bottom surface*.—Lightly pubescent.
*Leaf internode length*.—Approximately 1.1 cm.
*Color*.—Young foliage upper side: Near Green 137A. Young foliage under side: Near Green 137B. Mature foliage upper side: Near Green 137A. Mature foliage under side: Near Green 138A.
*Venation*.—Type: Palmately net. Venation color upper side: Near Yellow Green 144C. Venation color under side: Near Green 138B.
Petiole:
*Average length*.—Approximately 2.7 cm.
*Color*.—Near Green 138A.
*Diameter*.—Approximately 0.3 cm.

BLOOM

Inflorescence:
*Flowering habit*.—Induced by darkness period greater than 13.5 hours, approximately 49 days of appropriate day length required to induce and develop blooms.
*Inflorescence form*.—Decorative.
*Natural flowering season*.—Approximately the first two weeks of September.
*Number of inflorescences per lateral branch*.—Approximately 25.
*Inflorescence diameter*.—Approximately 6.9 cm.
*Inflorescence depth*.—3.4 cm.
*Inflorescence longevity on plant*.—Approximately 29 days.
*Persistence*.—Persistent.
Ray florets:
*Appearance*.—Matte.
*Texture*.—Smooth.
*Average number of ray florets per inflorescence*.—230.
*Shape*.—Oblong.
*Aspect*.—Flat.
*Margin*.—Entire.
*Apex*.—Obtuse.
*Length*.—Approximately 3.4 cm.
*Width*.—Approximately 1 cm.
*Color*.—Upper surface at first opening: Near Red-Purple 59D. Upper surface at maturity: Near Red-Purple 62C. Upper surface at fading: Near Red-Purple 62D. Under surface at first opening: Near Red-Purple 64B. Under surface at maturity: Near Yellow-White 158D. Under surface at fading: Near Red-Purple 68C.
Disc florets:
*Appearance*.—Shiny.
*Texture*.—Smooth.
*Average number of florets per disc*.—Approximately 10.
*Shape*.—Cylindric.
*Apex*.—Obtuse.
*Average length*.—Approximately 0.4 cm.
*Average width*.—Approximately 0.1 cm.
*Color*.—At first opening: Near Yellow-Green 154D. At maturity: Near Yellow 4C. At fading: Near Yellow-Orange 16B.
Peduncle:
*Length*.—At terminal end (shortest): Approximately 4.8 cm. At lateral end (longest): Approximately 8.2 cm.
*Angle to stem*.—Acute.
*Strength*.—Moderate.
*Color*.—Near Green 138B.
*Habit*.—Upright.
*Diameter*.—Approximately 0.2 cm.
*Surface texture*.—Lightly pubescent.
Inflorescence bud:
*Length*.—Approximately 1 cm.
*Diameter*.—Approximately 0.9 cm.
*Form*.—Globular.
*Color*.—Near Red-Purple 58A.
Involucral bracts (phyllaries):
*Appearance*.—Matte.
*Texture*.—Lightly pubescent.
*Number*.—Approximately 40.
*Shape*.—Oblanceolate.
*Margin*.—Entire.
*Apex*.—Acute.
*Length*.—0.9 cm.
*Width*.—0.8 cm.
*Color*.—Upper side: Near Green 138A. Under side: Near Green 138A.

REPRODUCTIVE ORGANS

Ray florets:
*Number of pistils per floret*.—1.
*Stigma shape*.—2 branched.
*Stigma color*.—Near Yellow 7A.
*Style color*.—Near Yellow 2C.
*Style length*.—0.8 cm.
*Stamens*.—Absent.
Disc florets:
*Number of pistils per floret*.—1.
*Stigma shape*.—Two branched.
*Stigma color*.—Near Yellow 2C.
*Style length*.—0.3 cm.
*Style color*.—Near Yellow-Green 154D.
*Number of stamens per floret*.—Approximately 5.
*Anther shape*.—Tubular.
*Anther color*.—Near Yellow 12C.
*Pollen color*.—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Not observed because commercially the plants are discarded or the flowers removed before seed set occurs.

What is claimed is:

1. A new and distinct cultivar of *Chrysanthemum* plant named 'PPP MIL PK05' as herein illustrated and described.

* * * * *